United States Patent
Czop et al.

(10) Patent No.: US 10,350,018 B2
(45) Date of Patent: Jul. 16, 2019

(54) STERILE RADIATION SHIELD DRAPE, COMBINATION OF A RADIATION SHIELD AND STERILE DRAPE THEREFOR AND METHOD OF PROVIDING A STERILE DRAPE ABOUT A RADIATION SHIELD

(75) Inventors: Michael W. Czop, Fenton, MI (US); Nathan M. Sokolowski, Flint, MI (US); Samba Toure, Grand Blanc, MI (US); Richard A. Weaver, Linden, MI (US); Terry M. Byers, Flushing, MI (US)

(73) Assignee: TIDI Products, LLC, Neenah, WI (US)

( * ) Notice: Subject to any disclaimer, the term of this patent is extended or adjusted under 35 U.S.C. 154(b) by 1535 days.

(21) Appl. No.: 13/008,291

(22) Filed: Jan. 18, 2011

(65) Prior Publication Data

US 2011/0174316 A1    Jul. 21, 2011

Related U.S. Application Data

(60) Provisional application No. 61/295,871, filed on Jan. 18, 2010.

(51) Int. Cl.
| | | |
|---|---|---|
| *A61F 5/37* | (2006.01) | |
| *A61B 46/00* | (2016.01) | |
| *A61B 90/50* | (2016.01) | |
| *A61B 90/00* | (2016.01) | |

(52) U.S. Cl.
CPC .............. *A61B 46/00* (2016.02); *A61B 90/50* (2016.02); *A61B 2090/0481* (2016.02)

(58) Field of Classification Search
CPC ....... A61B 19/081; A61B 19/10; A61B 19/08; A61B 19/12; A61B 46/00; A61B 46/10; A61B 46/13; A61B 46/17; A61B 46/20; A61B 2046/201; A61B 2046/205; A61B 46/23; A61B 204/234; A61B 2046/236; A61B 46/27; A61B 2046/234
USPC ................ 128/849, 852, 853, 854, 856, 855
See application file for complete search history.

(56) References Cited

U.S. PATENT DOCUMENTS

| | | | | |
|---|---|---|---|---|
| 3,777,749 | A * | 12/1973 | Collins ................... | A61B 46/00 128/855 |
| 4,166,461 | A * | 9/1979 | Oliver .................... | A61B 46/00 128/855 |
| 4,903,710 | A * | 2/1990 | Jessamine et al. ........... | 128/849 |
| 5,015,864 | A | 5/1991 | Maleki | |

(Continued)

FOREIGN PATENT DOCUMENTS

EP          1321947          6/2003

*Primary Examiner* — Victoria J Hicks
(74) *Attorney, Agent, or Firm* — Boyle Fredrickson, S.C.

(57) ABSTRACT

A sterile radiation shield drape configured to be disposed about a radiation shield while the radiation shield is hanging from a support at its top end and extending to a free bottom end is provided. The radiation shield drape includes a circumferentially continuous wall having a sterilized outer surface and an inner surface extending between an upper end and a lower end. The inner surface circumferentially bounds a cavity sized for receipt of the radiation shield. The upper end has an everted edge providing at least one pocket extending along the upper end and further includes at least one fastener provided adjacent the upper end. The at least one fastener is configured to releasably fix the circumferentially continuous wall about the radiation shield.

1 Claim, 13 Drawing Sheets

(56) References Cited

U.S. PATENT DOCUMENTS

| | | | |
|---|---|---|---|
| 5,015,865 A | 5/1991 | Sayers | |
| 5,115,140 A | 5/1992 | Rodriguez | |
| 5,379,703 A * | 1/1995 | Marshall | A61B 46/10 |
| | | | 108/90 |
| 7,343,919 B2 * | 3/2008 | Czajka | A61B 46/20 |
| | | | 128/849 |
| 7,543,587 B2 * | 6/2009 | Yardan et al. | 128/849 |
| 7,549,179 B1 | 6/2009 | Saied | |
| 8,188,453 B2 | 5/2012 | Kirschenbaum | |
| 8,716,687 B2 | 5/2014 | Goldstein et al. | |
| 2009/0184269 A1 | 7/2009 | Rees | |
| 2012/0167896 A1 * | 7/2012 | Stang | 128/849 |

* cited by examiner

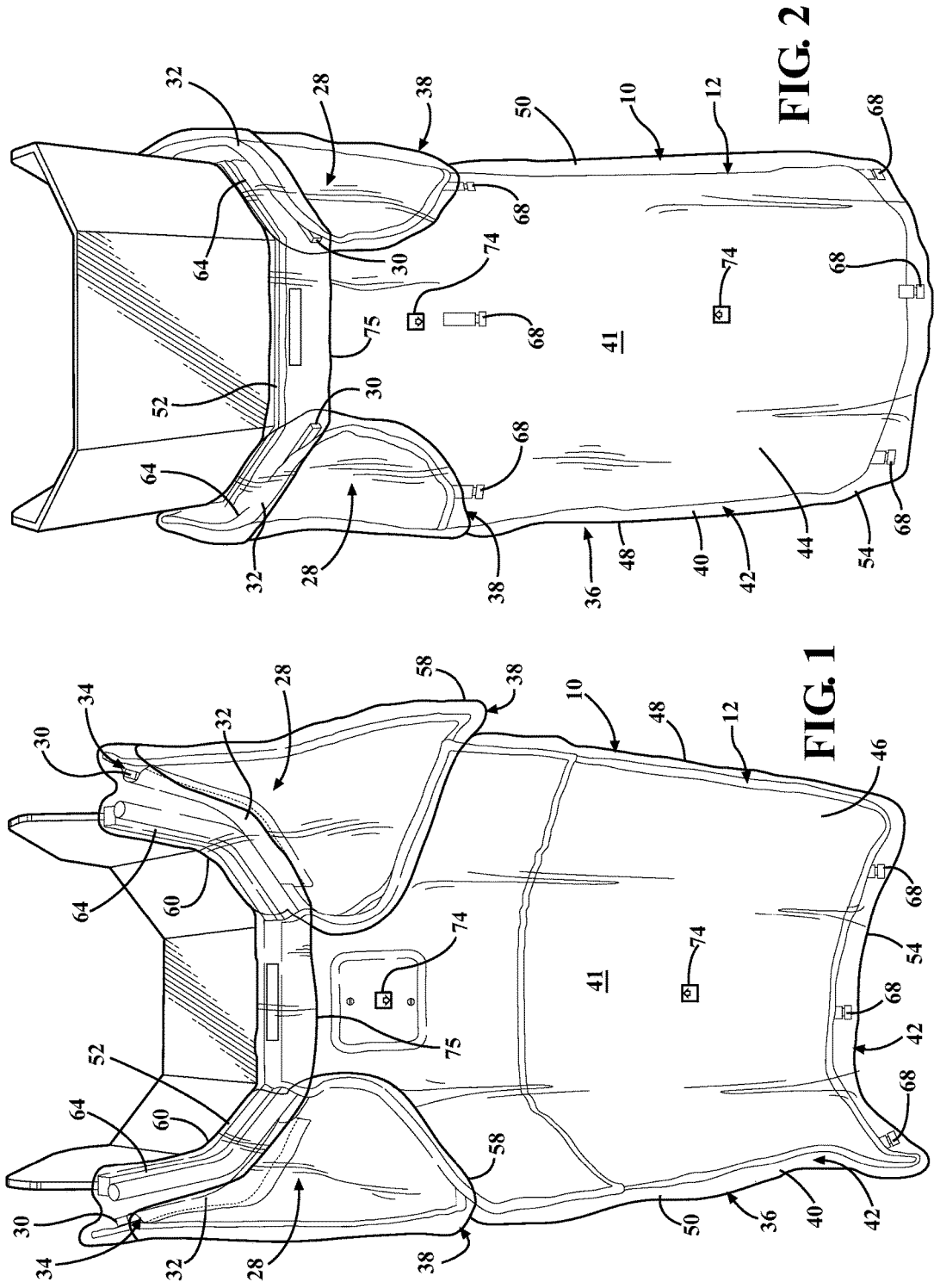

STERILE RADIATION SHIELD DRAPE, COMBINATION OF A RADIATION SHIELD AND STERILE DRAPE THEREFOR AND METHOD OF PROVIDING A STERILE DRAPE ABOUT A RADIATION SHIELD

CROSS-REFERENCE TO RELATED APPLICATION

This application claims the benefit of U.S. Provisional Application Ser. No. 61/295,871, filed Jan. 18, 2010, which is incorporated herein by reference in its entirety.

BACKGROUND OF THE INVENTION

1. Technical Field

This invention relates generally to sterilized drapes used in medical procedures, and more particularly to sterilized drapes configured to enclose radiation shields in medical procedures and to their method of installation.

2. Related Art

It is common to apply sterilized drapes to medical equipment used in medical procedures to prevent having to sterilize the equipment itself. The drapes present an external sterile surface to facilitate avoiding contaminating a patient. Though desirable to apply sterilized drapes to various types of medical equipment, it can prove challenging to apply the drapes to the equipment due to the configurations of the medical equipment and the drapes themselves, and further, it can prove difficult to avoid compromising the sterile external surface of the drapes during application. In addition, it can prove challenging to provide full and substantially unfettered use of the medical equipment upon applying the drapes to the equipment as a result of the drapes impeding movement of the equipment.

SUMMARY OF THE INVENTION

A sterile radiation shield drape configured to be disposed about a radiation shield while the radiation shield is hanging from a support at its top end and extending to a free bottom end is provided. The radiation shield drape includes a circumferentially continuous wall having a sterilized outer surface and an inner surface extending between an upper end and a lower end. The inner surface circumferentially bounds a cavity sized for receipt of the radiation shield. The upper end has an everted edge providing at least one pocket extending along the upper end and further includes at least one fastener provided adjacent the upper end. The at least one fastener is configured to releasably fix the circumferentially continuous wall about the radiation shield.

In accordance with another aspect of the invention, the drape has at least one flap attached to the wall, wherein the flap has a pocket configured to receive a portion of the radiation shield adjacent the upper end of the drape.

In accordance with another aspect of the invention, the drape has a plurality of fasteners on opposite sides of the upper end configured for operable attachment to the drape.

In accordance with yet another aspect of the invention, the drape has an everted edge at the upper end providing pockets to facilitate disposing the drape on the radiation shield.

In accordance with yet another aspect of the invention, the lower end of the drape is closed.

In accordance with another aspect of the invention, the sides of the shield are foldable to a circumferentially folded configuration of a known diameter and expandable outwardly from the folded configuration to an expanded configuration of a known maximum width.

In accordance with another aspect of the invention, a sterile radiation shield drape in combination with a radiation shield is provided. The radiation shield includes opposite top and bottom ends with opposite sides extending between the top and bottom ends. The radiation shield drape includes a circumferentially continuous wall having a sterilized outer surface and an inner surface extending between an upper end and a lower end. The inner surface circumferentially bounds a cavity sized for housing the radiation shield. The upper end has an everted edge providing at least one pocket extending along the upper end. At least one fastener is provided adjacent the upper end of the circumferentially continuous wall. The at least one fastener is configured to releasably fix the circumferentially continuous wall about the radiation shield.

In accordance with another aspect of the invention, a method of providing a sterile surface about a suspended radiation shield is provided. The method includes providing a circumferentially continuous flexible wall extending between an upper end and a lower end with the wall having a sterilized outer surface and an inner surface bounding a cavity sized for receipt of the suspended radiation shield. Further, attaching at least one fastener adjacent the upper end. Further yet, placing the upper end of the flexible wall beneath the suspended radiation shield within a sterile surgical region and disposing the suspended radiation shield in the cavity of the flexible wall by lifting the upper end of the flexible wall about the suspended radiation shield. Then fixing the at least one fastener relative to the suspended radiation shield to maintain the flexible wall in fixed relation about the suspended radiation shield.

In accordance with another aspect of the invention, the drape may also include a first flap that is adjacent the upper end. The first flap may include an outer panel defined by one or more outer panel edges and an inner panel defined by one or more inner panel edges. Additionally, the one or more inner panel edges may be affixed to the one or more outer panel edges to define a first flap cavity having an opening adjacent the upper end of the wall. Further still, the drape may also include a second flap that is also adjacent the upper end. The second flap may also include an outer panel defined by one or more outer panel edges and an inner panel defined by one or more inner panel edges. The one or more inner panel edges may be affixed to the one or more outer panel edges to define a second flap cavity having an opening adjacent the upper end of the wall.

In accordance with yet another aspect of the invention, the drape may also include at least one bag-shaped flap that is adjacent the upper end. The at least one bag-shaped flap may include an outer panel defined by one or more outer panel edges and an inner panel defined by one or more inner panel edges. Additionally, the one or more inner panel edges may be affixed to the one or more outer panel edges to define a flap cavity having an opening adjacent the upper end of the wall. Further still, the at least one bag-shaped flap may be attached adjacent the upper end of the wall and the flap cavity may be configured to receive a shoulder shield portion of the radiation shield.

In accordance with another aspect of the invention, the drape may also include an outer surface of the inner panel of the first flap that is affixed to the sterilized outer surface of the wall. Additionally, an outer surface of the inner panel of the second flap may be affixed to the sterilized outer surface of the wall.

In accordance with another aspect of the invention, an outer surface of the inner panel of the at least one bag-shaped flap is affixed to the sterilized outer surface of the wall.

In accordance with yet another aspect of the invention, the drape may further include a first flap at a first side of the upper edge of the wall that may include an outer panel defined by one or more outer panel edges and an inner panel defined by one or more inner panel edges. An outer surface of the inner panel of the first flap may be affixed to the sterilized outer surface of the wall. Additionally, the one or more inner panel edges may be affixed to the one or more outer panel edges to define a first flap cavity configured to receive a first shoulder shield portion of the radiation shield therein. Also, the first flap cavity may have an opening adjacent the upper end of the wall. Further still, the drape may include a second flap at a second side of the upper edge of the wall, opposite the first side. The second flap may include an outer panel defined by one or more outer panel edges and an inner panel defined by one or more inner panel edges. Also, an outer surface of the inner panel of the second flap may be affixed to the sterilized outer surface of the wall. Further yet, the one or more inner panel edges may be affixed to the one or more outer panel edges to define a second flap cavity that is configured to receive a second shoulder shield portion of the radiation shield therein. Also, the second flap cavity may have an opening adjacent the upper end of the wall.

BRIEF DESCRIPTION OF THE DRAWINGS

These and other aspects, features, and advantages of the invention will become more readily appreciated when considered in connection with the following detailed description of presently preferred embodiments and best mode, appended claims and accompanying drawings, in which:

FIG. 1 is a rear view of a sterilizable drape constructed in accordance with one aspect of the invention disposed on a radiation shield;

FIG. 2 is a front view of the sterilizable drape assembled on the radiation shield of FIG. 1;

DETAILED DESCRIPTION OF PRESENTLY PREFERRED EMBODIMENTS

Figure 3:
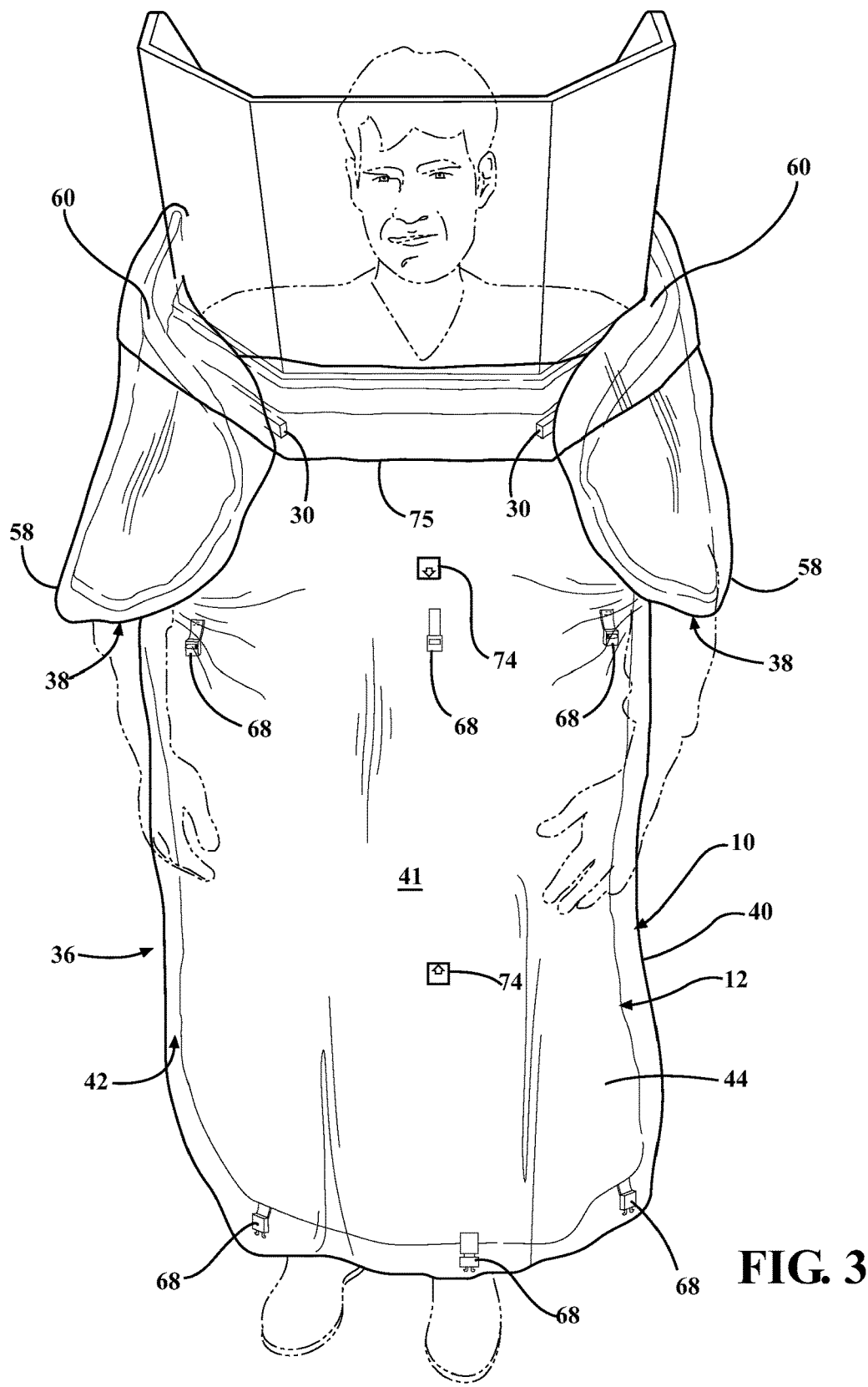
FIG. 3 is a view similar to FIG. 2 showing the radiation shield with the sterilizable draped disposed thereon being worn by a user.

Referring in more detail to the drawings, FIGS. 1 and 2 illustrate rear and front views, respectively, of a flexible sterile radiation shield drape, referred to hereafter as drape 10, constructed in accordance with one aspect of the invention disposed over a radiation shield, referred to hereafter as shield 12, with the shield being shown in an open position. In FIG. 3, the shield 12 is shown wrapped in a circumferentially folded configuration about a user's torso, with the drape 10 being maintained in conformity with the shield 12, thereby being contoured or substantially contoured to the user's body. The drape 10 is configured to be disposed over the shield 12 in a bottom-to-top installation process that allows the drape 10 to conform or substantially conform to the shield 12 without compromising the sterility of the outer sterile drape surfaces. As such, with the drape 10 being conformed to the shape of the shield 12, a user is able to retain maximum degrees of movement without interference from the drape 10. Further, the flexible drape 10 allows the shield 12 to maintain its full range of unimpeded movement as though the drape 10 were not present. In addition, the drape 10 is provided as a one-piece assembly, thereby keeping the number of components having to be handled to provide a sterile barrier about the shield 12 to a minimum.

Figure 4:
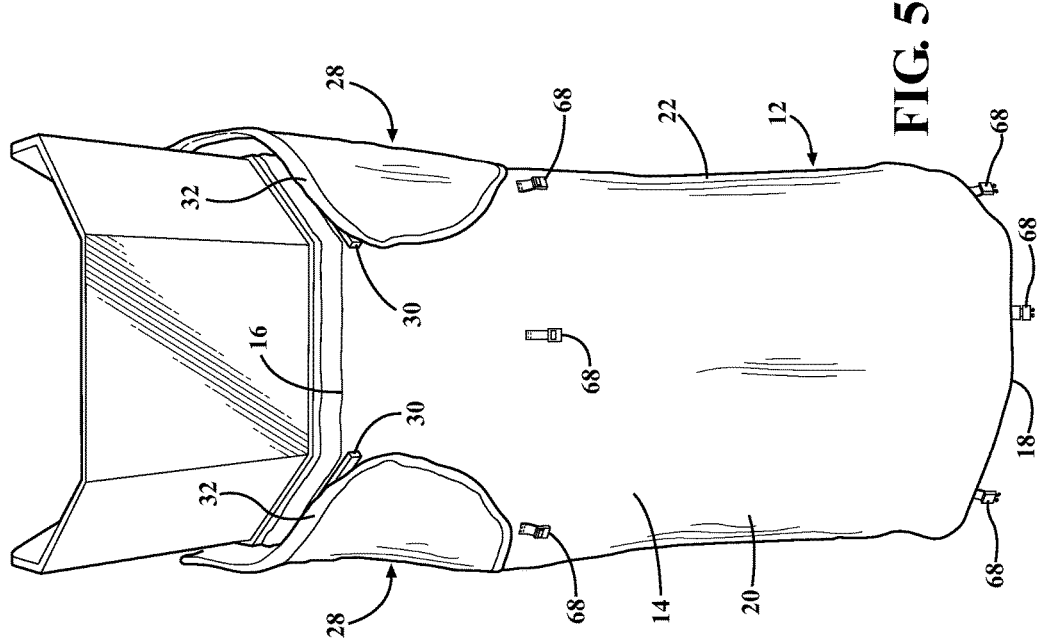
FIG. 4 is a rear view of the radiation shield shown in an extended and unwrapped configuration.
Figure 5:
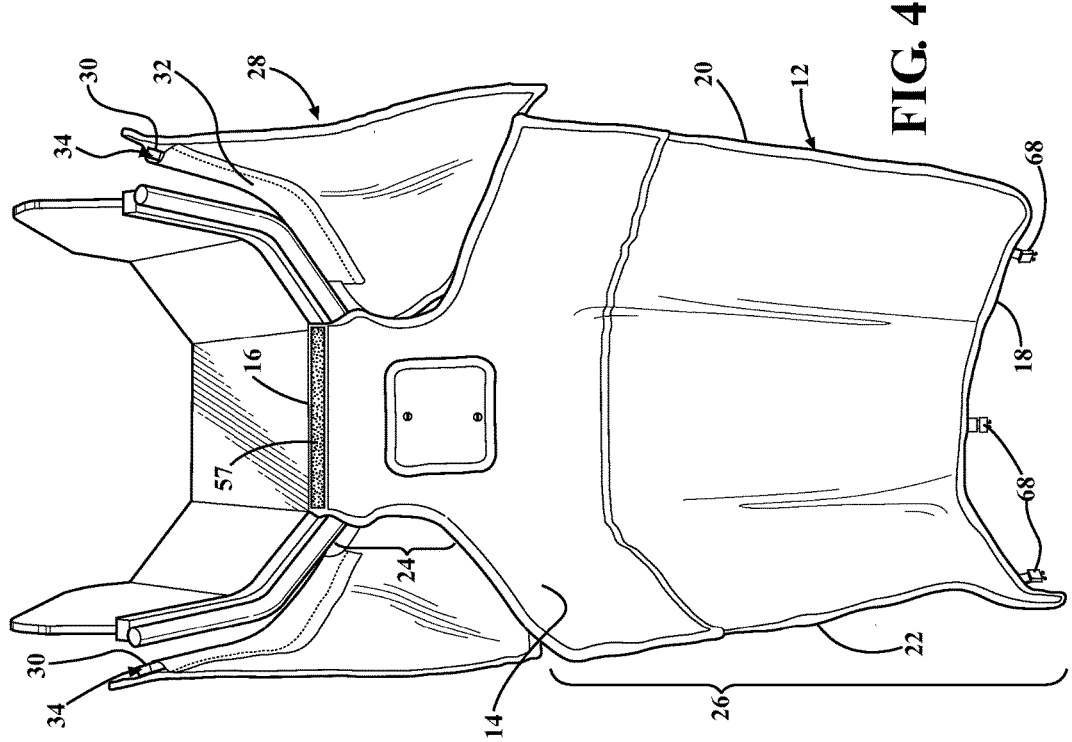
FIG. 5 is a front view of the radiation shield of FIG. 4.
Figure 6:
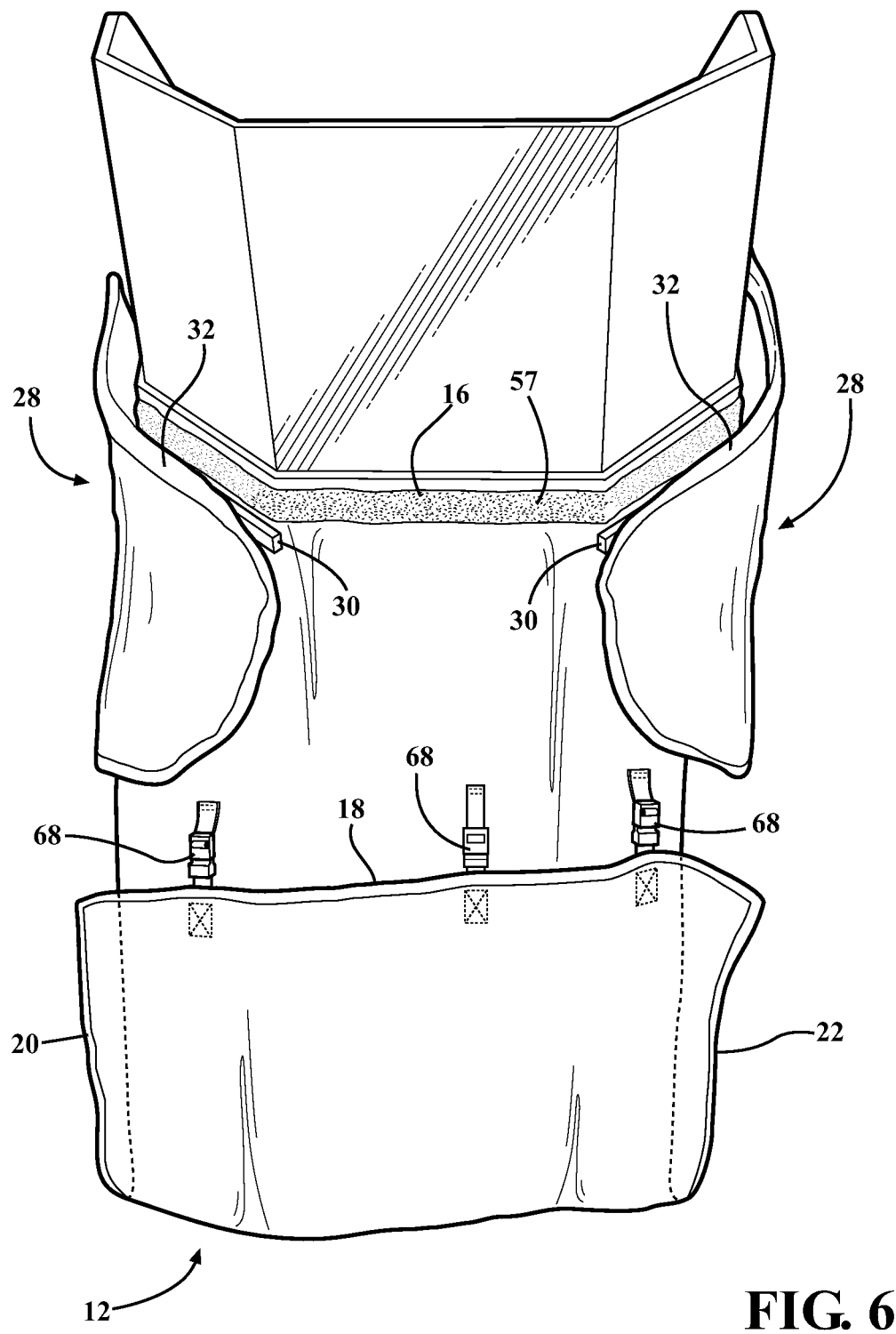
FIG. 6 is a front view of the radiation shield of FIG. 5 shown in a vertically folded configuration.
Figure 7:
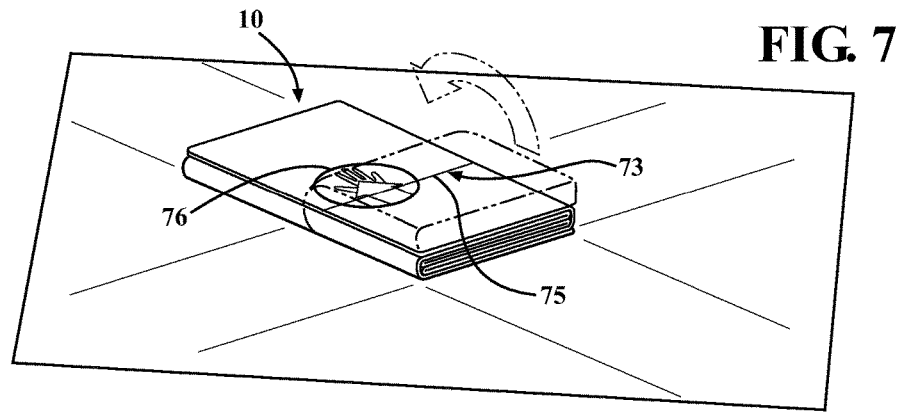
FIGS. 7-11A show various stages of the sterilized drape being unfolded from an as packaged, folded state.
Figure 8:
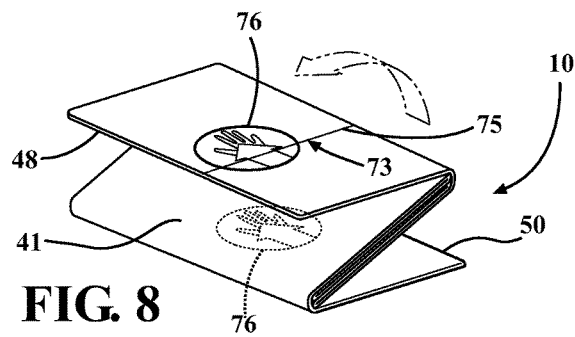
Figure 9:
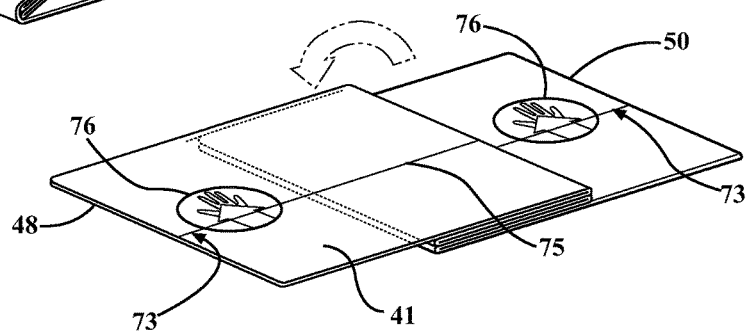
Figure 10:
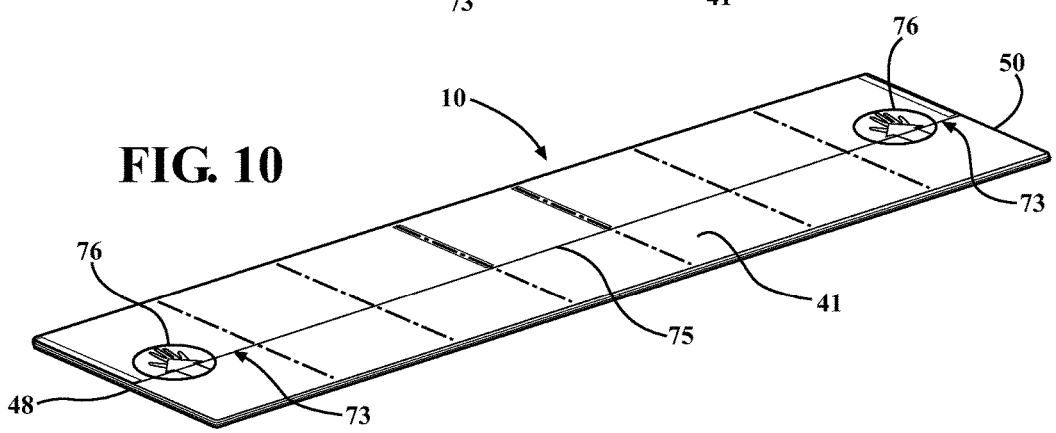

As best shown in FIGS. 4-6, the shield 12 has a main body identified generally at 14 with opposite top and bottom ends, also referred to as upper and lower ends 16, 18, respectively, with laterally spaced sides 20, 22 extending between the ends 16, 18. The body 14 can be supported by a suspending mechanism, such as shown wherein the suspending mechanism is operably attached to the upper end 16 with the shield 12 hanging freely therefrom to its free lower end 18, for example; can be constructed of any suitable material capable of acting as a barrier to radiation, such as lead or a leaded material, for example, and can have an internal frame structure, such as disclosed in U.S. patent application Ser. No. 12/099,077 filed on Apr. 7, 2008, which is incorporated herein by reference in its entirety. The internal frame structure of the shield 12 are provided as horizontally extending (generally parallel to a floor surface) foldable members that can be readily folded by the user, as desired, to wrap the sides 20, 22 circumferentially toward one another to enclose or substantially enclose the sides of the user's body with the shield 12. The foldable members can be configured to remain in their folded configuration via friction at the respective pivot joints of the foldable members, and thus, upon being folded or pivoted, the foldable members tend to remain in their desired folded orientation until acted on by a suitable external force to intentionally move the foldable members to their unfolded, extended position, such as shown in FIGS. 1, 2, 4 and 5. Accordingly, the foldable members can be folded inwardly toward one another and outwardly away from one another, as desired by the user, to allow the shield 12 to be selectively wrapped about the user and unwrapped from the user.

As best shown in FIG. 4, the shield 12 has an upper reduced width region 24 extending upwardly from a lower increased width region 26. The upper reduced width region 24 is intended to extended along the user's chest or sternum toward the neck region of the user to a central portion of the upper end 16, as shown in FIG. 3, to allow full and unfettered movement of the user's arms, such as may be necessary during a surgical procedure. The lower increased width region 26 of the shield 12 has a generally uniform rectangular shape, by way of example, bounded by the sides 20, 22, the lower end 18 and outer portions of the upper end 16. The lower increased width region 26 has the aforementioned foldable members extending generally from one side 20 to the other side 22 to allow the lower region 26 to be folded or wrapped in a circumferential direction at least partially about the user's body, as discussed.

The shield 12 can further include at least one, and shown here as a pair of laterally spaced shoulder shield portions or covers, also referred to as shoulder extension portions 28. The shoulder extension portions 28, by way of example and without limitation, are shown here as being detached from the main body 14 and supported in a hanging fashion from a support frame member 30 of the aforementioned suspending mechanism. When in place, the shoulder extensions 28 cover the user's shoulder region, while at the same time allow the user to retain full flexibility and freedom of movement in that the shoulder extension portions 28 are able to move freely with the movement of the user's shoulders and arms. The shoulder extension portions 28 are represented, by way of example and without limitation, as being generally triangular in shape, with one edge or side 32 of each extension 28 having a receptacle or elongate pocket 34 (FIGS. 1 and 4) for receipt of the supporting frame member 30.

The drape 10, as best illustrated in FIGS. 1-3, 11 and 11A, includes a main body identified generally at 36 configured to receive the body 14 of the shield 12 and a corresponding number of flaps, shown here as a pair of, laterally spaced flaps 38, configured to receive the shoulder extension portions 28 of the shield 12. The flaps 38 are provided to accommodate the number of shoulder extensions 28 on the shield 12, and thus, it should be recognized that the drape 10 could be constructed having one or no flaps, if desired. Further, to facilitate handling, among other things, the flaps 38 are attached to the main body 36, such as by a suitable adhesive, tape, fastener (e.g. hook and loop), or weld joint, identified generally at 77, for example, and thus, the drape 10 can be handled as a single piece of material.

Figure 11:
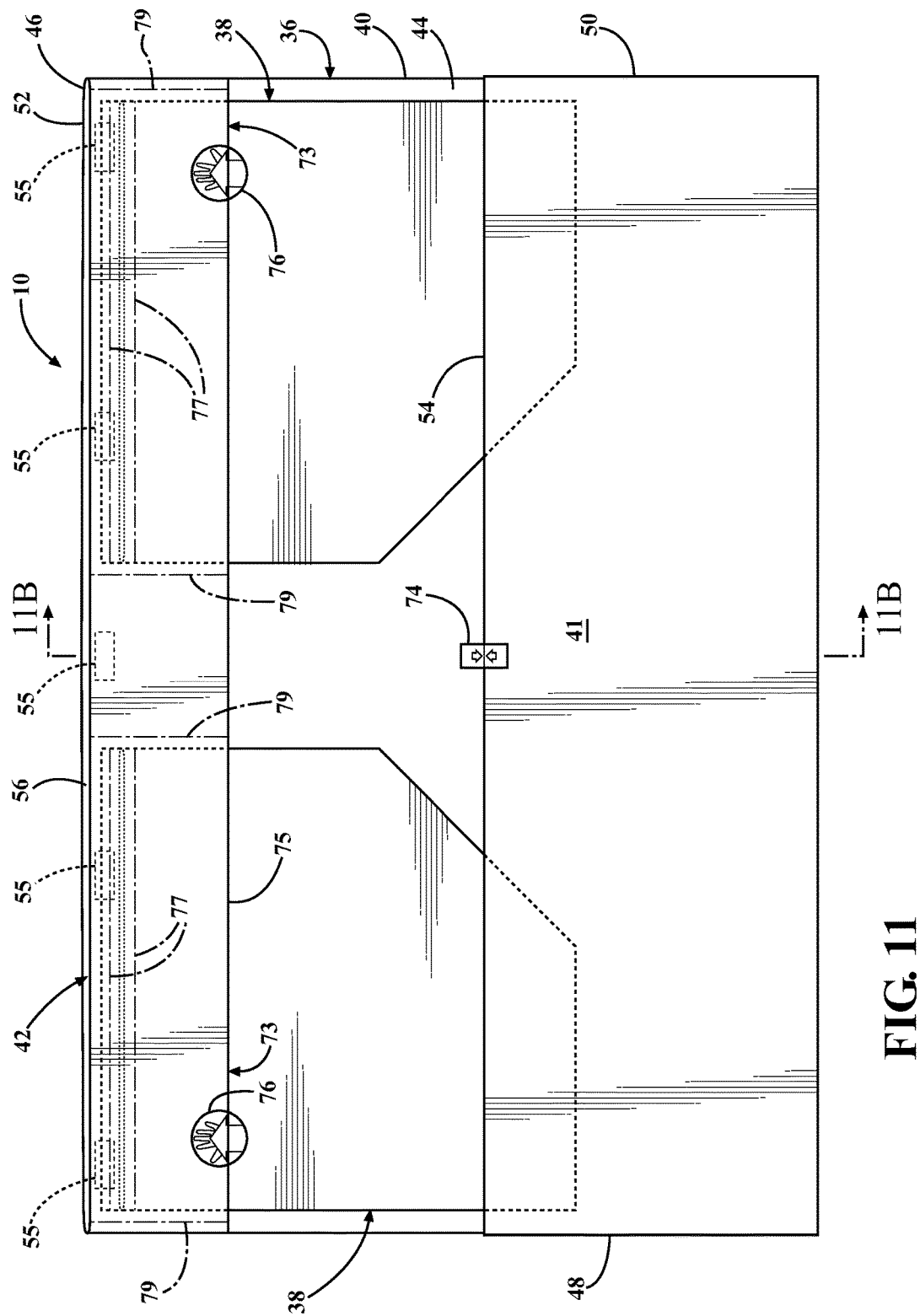
Figure 11A:
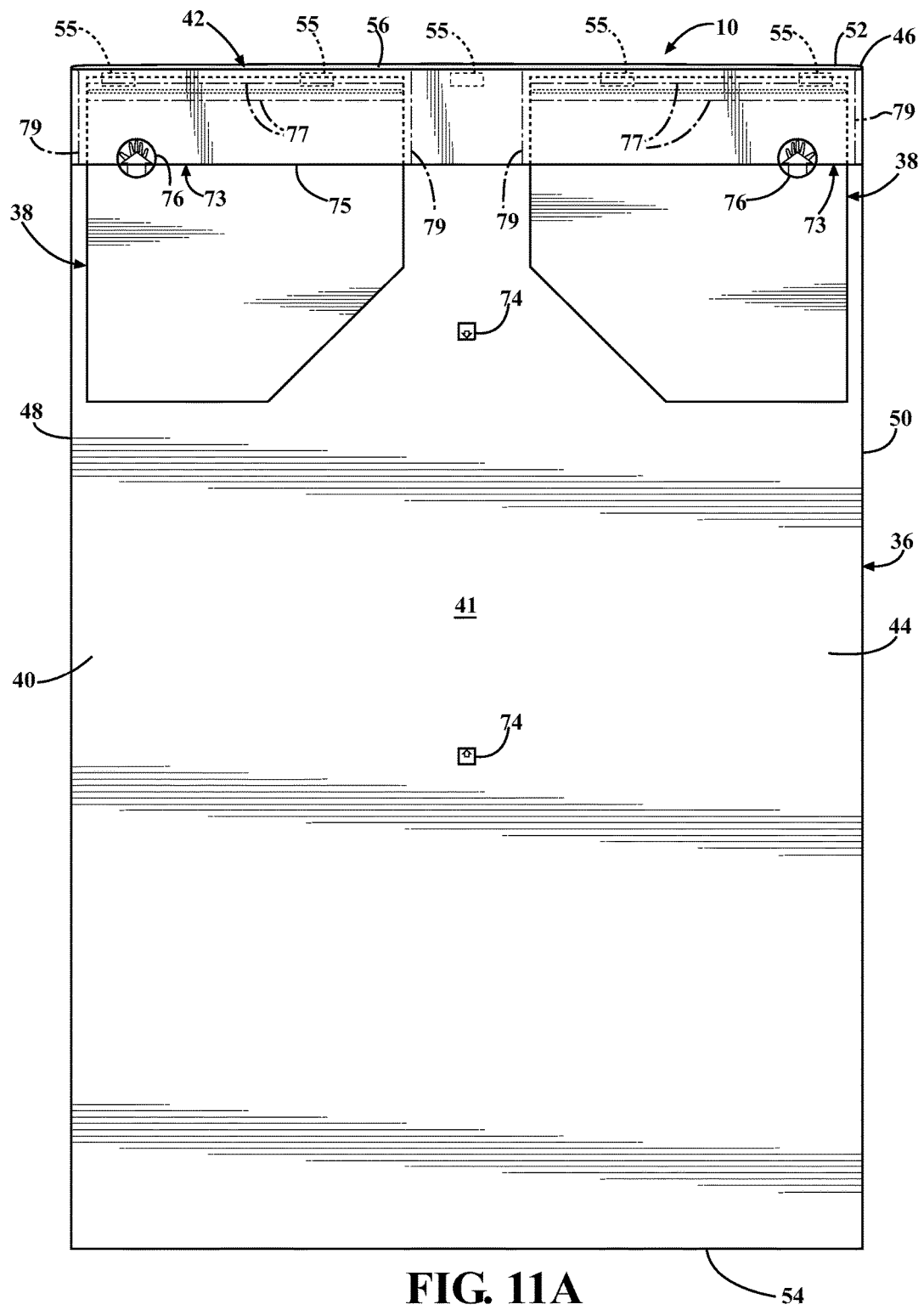
Figure 11B:
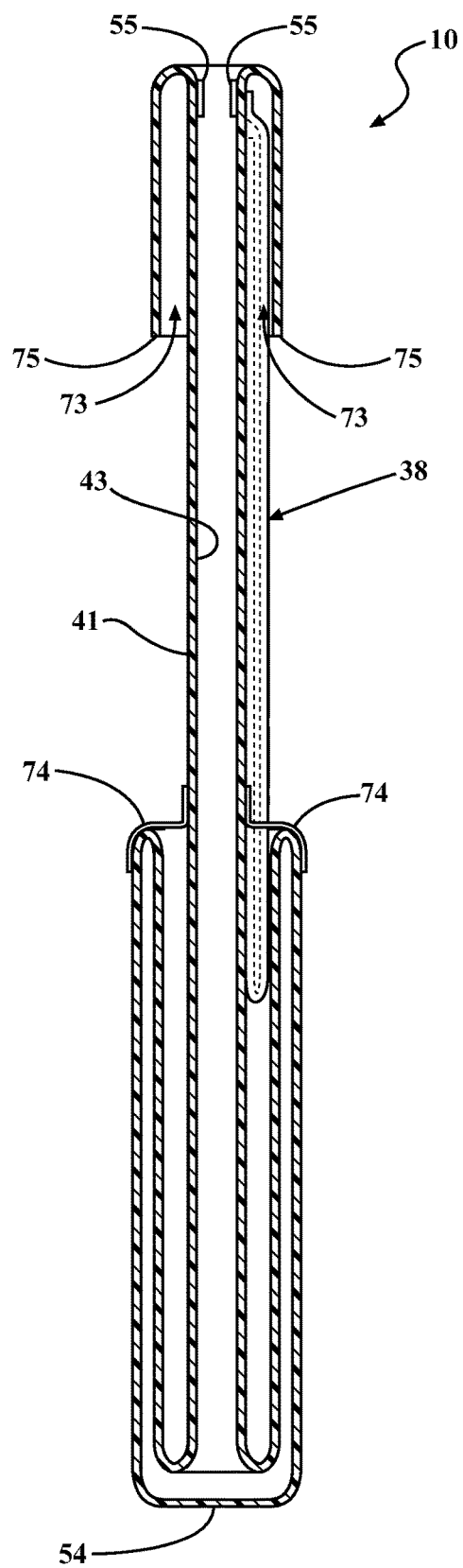
FIG. 11B is a cross-sectional view taken generally along the line 11B-11B of FIG. 11.
Figure 12:
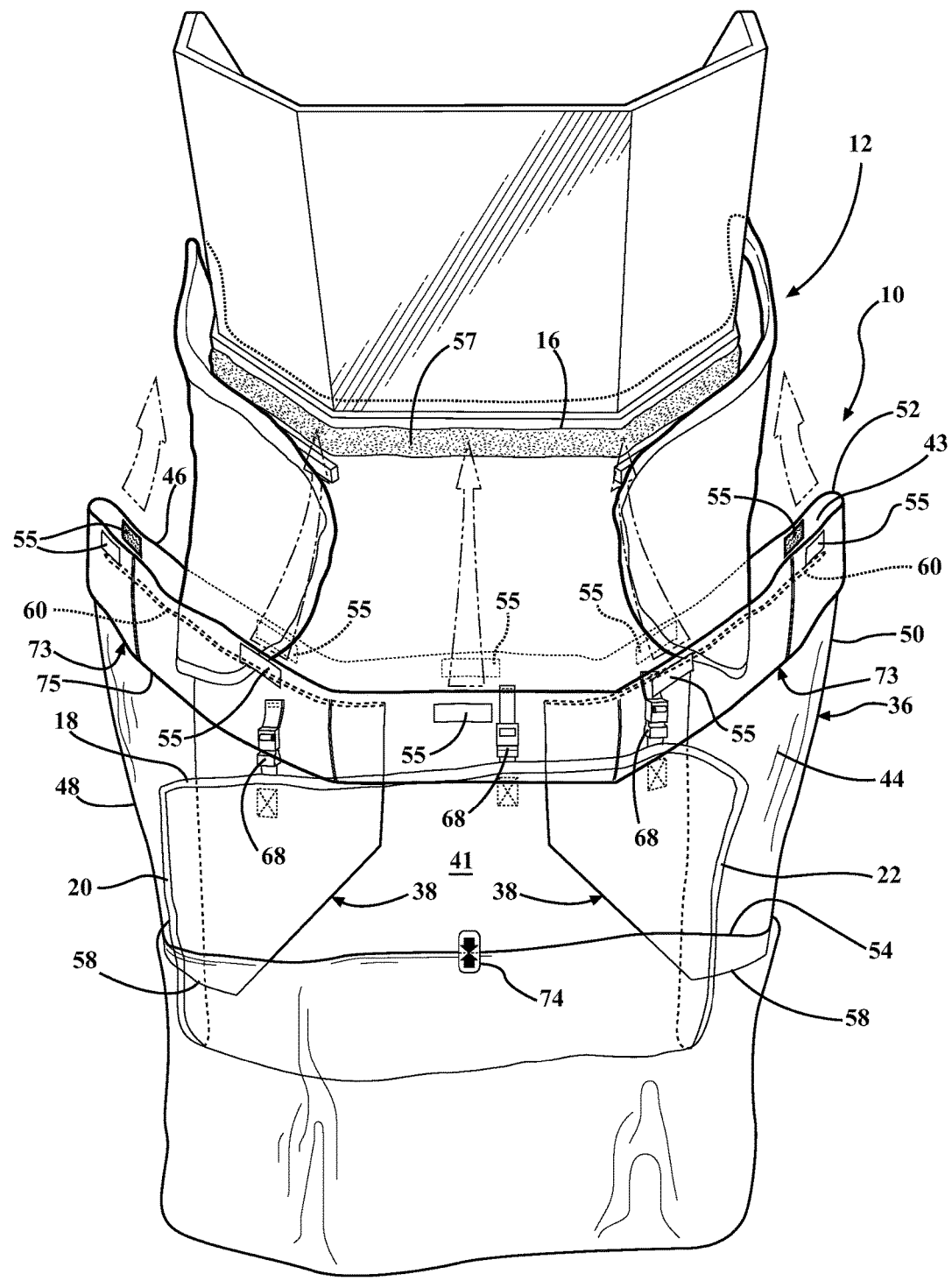
FIG. 12 is a front view of the radiation shield with the sterilized drape being initially disposed thereon.

The main body 36 has a generally tubular, flexible wall 40 with a sterilized outer surface 41 and a sterilized inner surface 43 that circumferentially encloses a cavity 42 sized for, receipt of the shield body 14 therein. As such, the wall 40 has opposite front and rear faces 44, 46, respectively, which can either be formed integrally with one another as a seamless, circumferentially continuous piece of material or separate pieces of material can be attached to one another along laterally spaced sides 48, 50, for example, that extend between upper and lower ends 52, 54 and along the lower end 54. Accordingly, the front and rear faces 44, 46 can be initially constructed as separate pieces of material, and subsequently attached to one another, such as via a heat weld or suitable adhesive, for example, to form the one-piece body 36. Further, it should be recognized that the wall 40 could be constructed as a single sheet of material having opposite edges folded into abutment with one another and subsequently attached to one another, if desired. To facilitate disposing the drape 10 on the shield 12, as best shown in FIGS. 11 and 11A, the upper end 52 has an opening 56 sized to receive the shield 12 while in its fully or substantially fully expanded state. The opening 56 extends completely across the upper end 52 from one side 48 to the opposite side 50. To facilitate releasably and operably fixing the drape 10 about the shield 12, a plurality of fasteners 55, such as one portion of the hook and loop-type fastener, for example, are attached adjacent the upper 52, wherein as shown, for example, five such fasteners 55 are attached along an inner portion of the front face 44 and five such fasteners 55 are attached along an inner portion of the rear face 46. It should be recognized that a corresponding number of fasteners, or a single elongate fastener 57, configured for releasable attachment to the fasteners 55 are provided adjacent the upper end 16 of the shield 12, such as the other portion of the hook and loop-type fastener, for example, wherein the fastener(s) 57 can be provided directly on the shield 12 and/or on the frame member 30 supporting the shield 12.

The flaps 38 are constructed having a generally triangular shape to conform or substantially conform in shape with the shoulder extension portions 28. The flaps 38 are generally bag-shaped having a closed end 58 and an opposite open end 60. The open end 60 provides an opening sized to receive the shoulder extension portions 28 therein.

Figure 13:
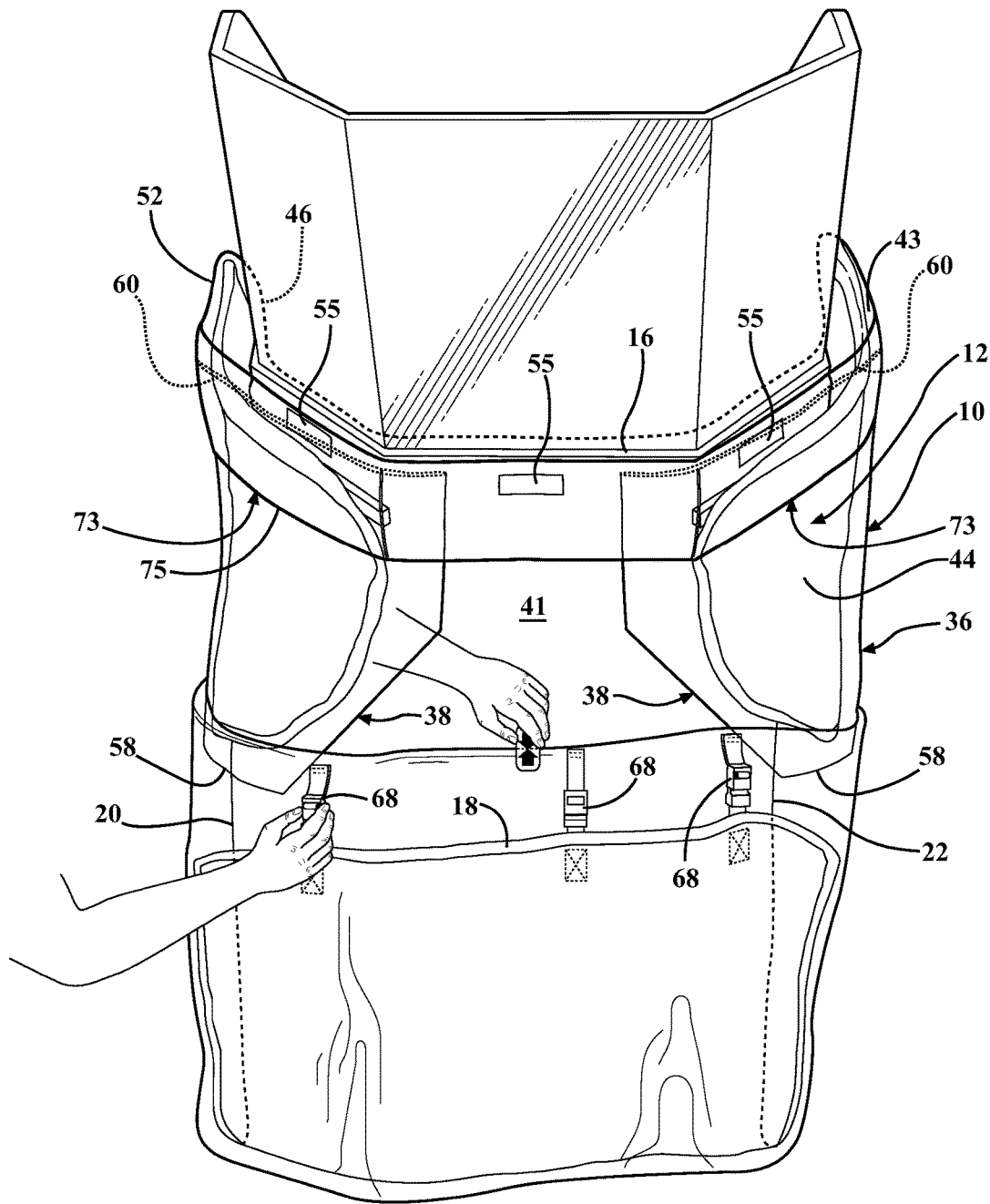
FIG. 13 illustrates a continuation of the assembly of the sterilized drape on the radiation shield from FIG. 12 while remaining in its vertically folded configuration.

Upon disposing the drape 10 on the shield 12 in a bottom-to-top installation process and detaching the lower end 54 of the drape 10 from the mid-section of the drape outer surface, the shield 12 can be readily unfolded circumferentially to bring the sides 20, 22 of the shield 12 into conformity or substantial conformity with the sides 48, 50 of the drape 10. Further, the shield 12 can then be unfolded vertically to its full length by unfastening clips 68 retaining the shield 12 in its folded configuration, such as shown in FIG. 13. The clips 68 can be readily unclasped by manipulating the clips 68 though they are covered by the drape 10.

Figure 15:
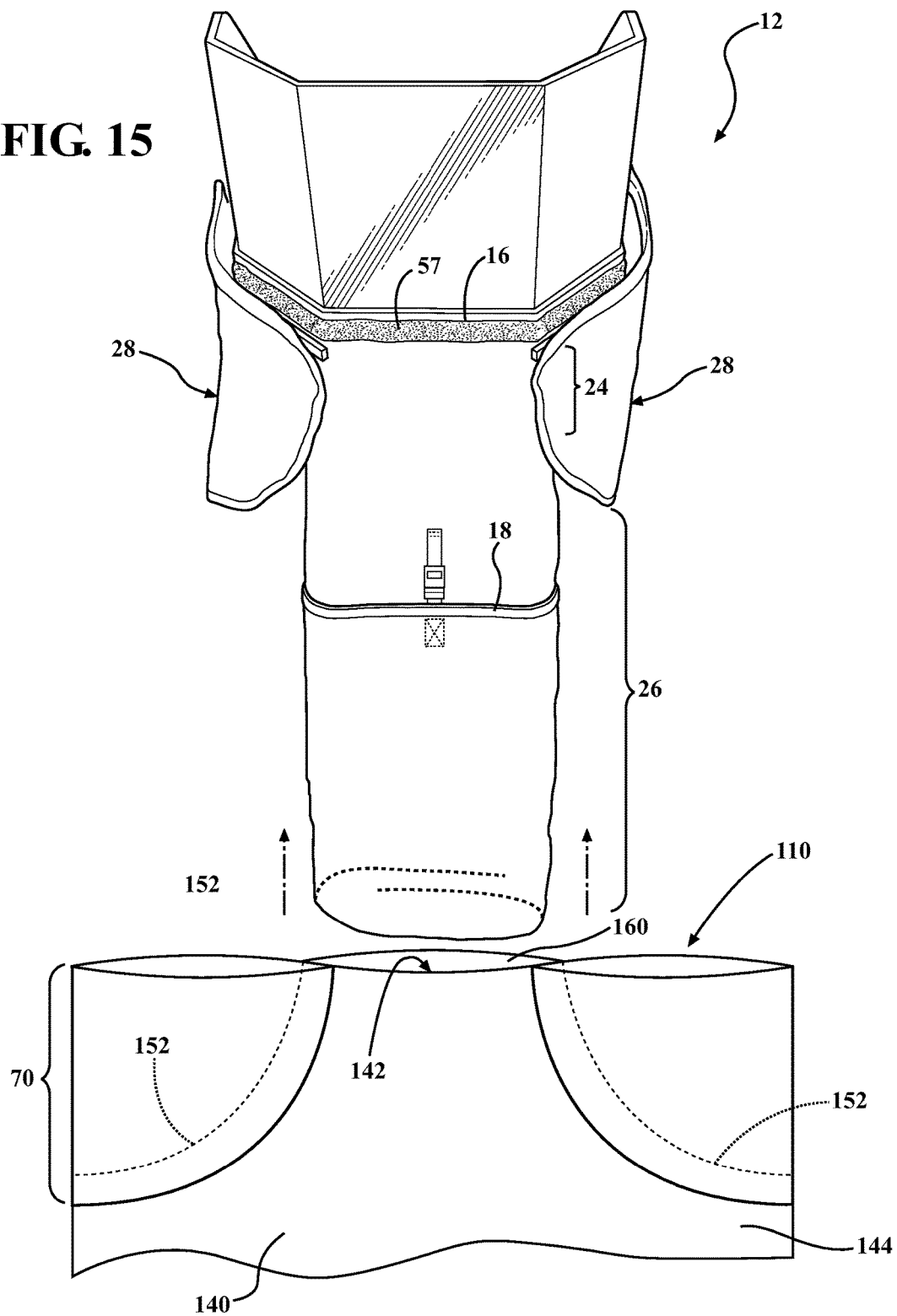
FIG. 15 is a partial view of a sterilized drape constructed in accordance with another aspect of the invention being positioned for disposal about the radiation shield.
Figure 16:
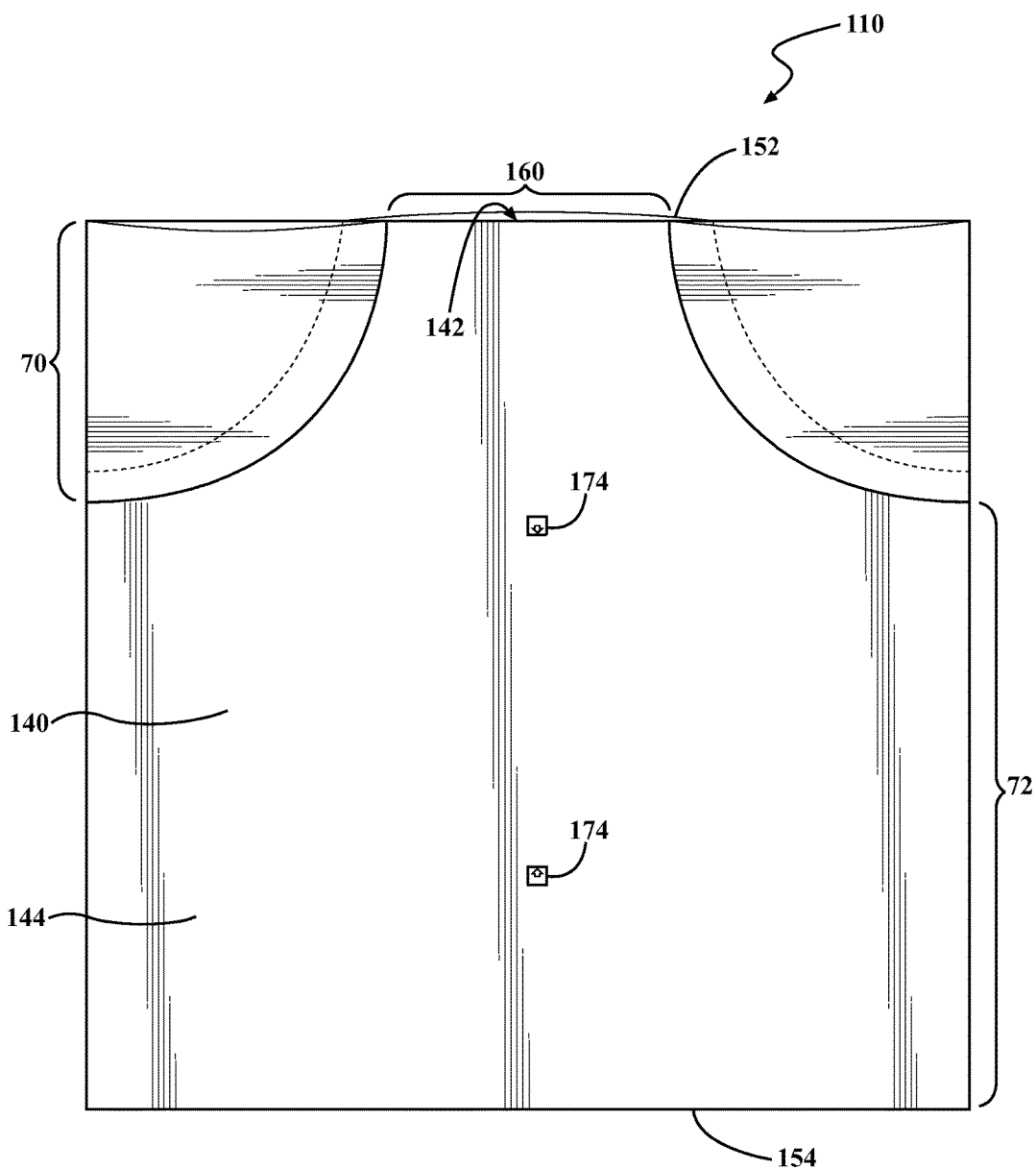
FIG. 16 is a front view of the sterilizable drape of FIG. 15.

As shown in FIGS. 15 and 16, a drape 110 constructed in accordance with another aspect of the invention is shown, wherein the same reference numerals, offset by a factor of 100, are used to illustrate like features. The drape 110 has a wall 140 with an upper reduced width region 70 extending upwardly from a lower increased width region 72. The upper reduced width region 70 conforms or substantially conforms in shape with the reduced width region 24 of the shield 12 and the lower increased width region 58 conforms or substantially conforms in shape with the increased width region 26 of the shield 12. An opening 160 extends across completely or substantially across an upper end 152 of the reduced width region 56, but does not extend across the upper end 152 of the lower increased width region 58. As such, the upper end 152 of the lower increased width region 58 remains sealed or closed via attachment of a front face 144 to a rear face of the main body 136. Accordingly, other than the opening 160, the cavity 142 inside the body 136 is closed off from the external environment. As such, in order to dispose the shield 12 in the cavity 142 through the opening 160, given the opening 160 has a smaller width relative to the expanded width of the shield 12, the shield 12 must be folded to its wrapped configuration in order to dispose the shield 12 through the opening 160. Then, upon disposing the shield 12 in the cavity 142, the shield 12 is unfolded to its expanded form, thereby bringing the shield 12 into conformity with the drape 110. Accordingly, unlike the previous drape 10 which results in drape material extending beyond the recesses formed at the junction of the reduced width region 24 and the increased width region 25 of the shield 12, the drape 110 follows or substantially follows the contour of the shield 12 in this region of the shield 12. Otherwise, aside from the differing geometry of the upper end 116 of the drape 110 from the upper end 16 of the drape 10, the drape 110 is generally the same as discussed above with regard to the drape 10.

In accordance with another aspect of the invention, a method of providing a sterile drape about a suspended radiation shield is provided. The method, with reference to the features discussed and identified above with reference numerals, includes removing, the sterilized, drape 10, 110 from a sterile package, and partially unfolding the drape 10, 110 as shown in FIGS. 7-11. During the initial unfolding of the drape 10, 110, the user places their hands in pockets 73 provided by an everted free edge 75 of the wall 40 extending circumferentially about the upper end 52 adjacent the opposite sides 48, 50 clearly identified by symbols of hands 76, for example, and laterally expands their arms to unfold the drape 10, 110 widthwise. The upper end 52 is maintained in its everted configuration via a fastening mechanism, such as a suitable adhesive or weld joint identified generally at 79. The upper end 52, 152 of the drape 10, 110 is then place beneath the lower end of the shield 12 with the shield in its vertically folded position. If using the drape 110, the shield 12 is also circumferentially folded in its wrapped configuration. With the opening 56, 156 aligned with the lower end 18 of the shield, the drape 10, 110 is then lifted to allow an upper portion, such as about ½ the length of the drape 10, 110 extending above fasteners 74 that releasably fix the lower end 54, 154 of the drape 10, 110 to an approximate midsection or region of the drape body 14, 114 located between the upper and lower ends 52, 54, to unfold lengthwise while maintaining the lower portion of the drape 10, 110 folded lengthwise as a result of the fasteners 74 position on the opposite sides 48, 50. As such, the folded lower end 54, 154 of the drape 10, 110 is readily maintained within the sterile surgical field during assembly about the shield 12, wherein, the sterile surgical field typically begins at a height of the operating table and extends upwardly therefrom, wherein the zone below the operating table is typically consider non-sterile. Then, upon lifting the upper end 52, 152 of the drape 10, 110 about the shield 12, the respective fasteners 55, 57 are fixed to one another to maintain the upper end 52, 152 in the desired fixed location about the upper end 16 of the shield 12.

Then, with the drape 10, 110 held in place about the shield 12 by the fasteners 55, 57, the fasteners 74, 174 are then detached, such as by tearing the fasteners, for example, to release the lower end 54, 154 from its folded position. Accordingly, the lower end 54, 154 is free to fall to its fully extended length, thereby unfolding the remaining sterile outer surface 41 which remains sterile. Then, the shield 12 is extended to its fill length by uncoupling the clips 68, thereby allowing the lower end 18 of the shield 12 to fall within the fully enclosed lower portion of the drape 10, 110.

Figures 14, 14A:
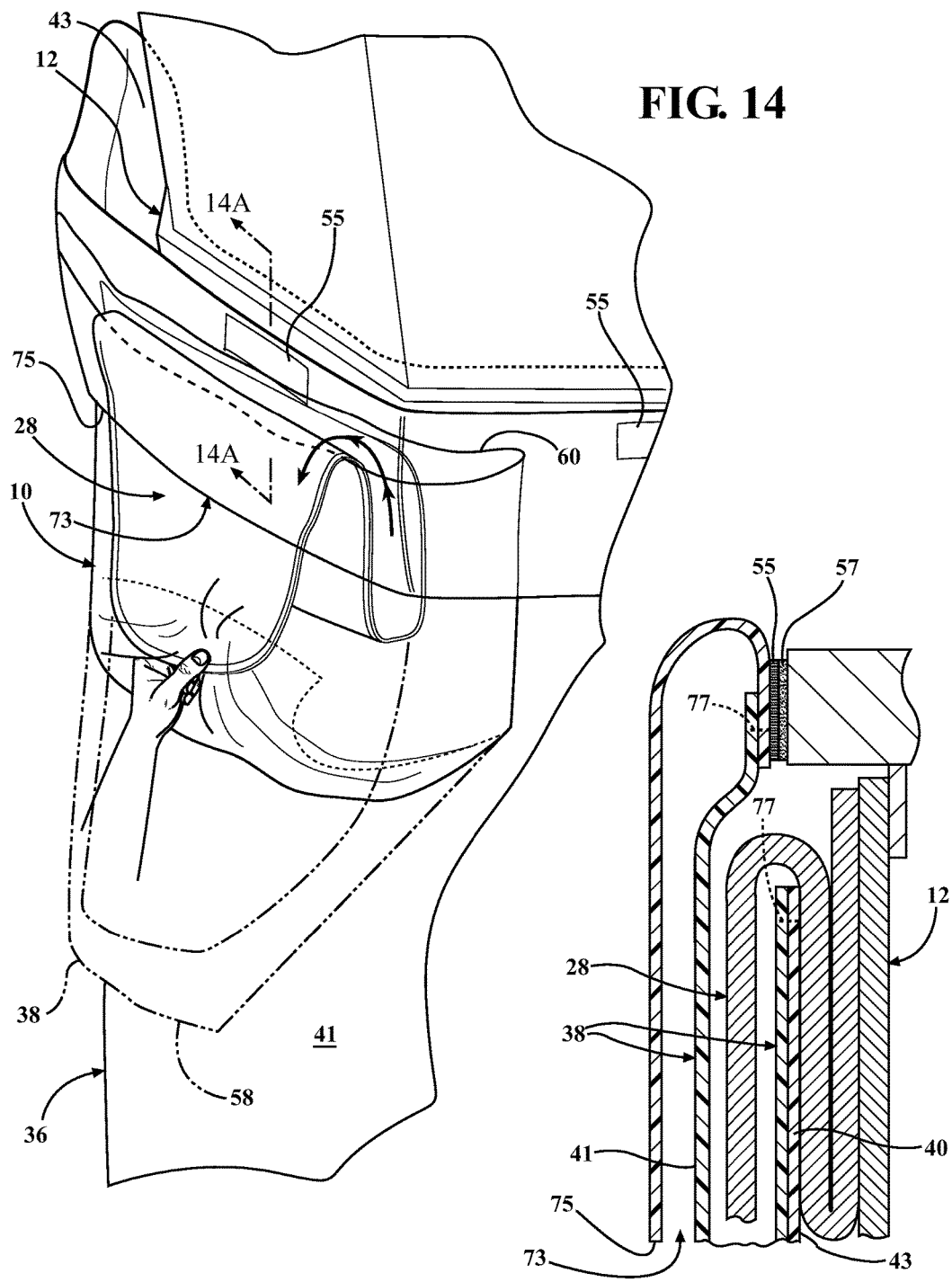
FIG. 14 is a partial view of the radiation shield and sterilized drape showing a shoulder extension portion being disposed in a pocket of a flap of the sterilized drape.
FIG. 14A is a cross-sectional view taken generally along the line 14A-14A of FIG. 14.

Then, as best shown in FIG. 14, if provided, the shoulder extension portions 28 of the shield 12 are disposed in the corresponding flaps 38 of the drape 10, 110.

Obviously, many modifications and variations of the present invention are possible in light of the above teachings. It is, therefore, to be understood that within the scope of the appended claims, the invention may be practiced otherwise than as specifically described.

What is claimed is:

1. A sterile radiation shield drape configured to be disposed about a radiation shield while the radiation shield is hanging from a support at its top end and extending to a free bottom end, said sterile radiation shield drape comprising:
   a wall having a sterilized outer surface and an inner surface extending between an upper end and a lower end, said upper end having an opening that extends completely across the upper end from a first side to a second side, said opening having a cavity extending downwardly therefrom; said inner surface configured to circumferentially define a cavity sized for receipt of the radiation shield when said wall is affixed about an outer surface of the radiation shield, said upper end having an everted edge providing at least one pocket extending along said upper end;
   at least one first fastener adjacent said upper end, said at least one first fastener being attached directly to said inner surface and configured for releasable attachment to the radiation shield to releasably fix said wall about the radiation shield;
   a first flap at the first side of the upper end of the wall, comprising:
      an outer panel defined by one or more outer panel edges,
      an inner panel defined by one or more inner panel edges, wherein an outer surface of the inner panel of the first flap is affixed to the sterilized outer surface of the wall,
      the one or more inner panel edges affixed to the one or more outer panel edges to define a first flap cavity configured to receive a first shoulder shield portion of the radiation shield therein, the first flap cavity having an opening adjacent the upper end of the wall; and
   a second flap at the second side of the upper end of the wall, opposite the first side, comprising:
      an outer panel defined by one or more outer panel edges,
      an inner panel defined by one or more inner panel edges, wherein an outer surface of the inner panel of the second flap is affixed to the sterilized outer surface of the wall,
      the one or more inner panel edges affixed to the one or more outer panel edges to define a second flap cavity configured to receive a second shoulder shield portion of the radiation shield therein, the second flap cavity having an opening adjacent the upper end of the wall;
         wherein said first flap has a closed lower end opposite said opening that extends completely across said upper end of said wall;
   wherein said second flap has a closed lower end opposite said opening that extends completely across said upper end of said wall;
   wherein said wall has a full length, unfolded state and a reduced length, folded state, said lower end being detachably affixed about a mid-section of said sterilized outer surface of said wall while in said reduced length, folded state;
   wherein the wall is configured to be installed initially about the free bottom end of the shield and then unfolded vertically upwardly toward the top of the drape when the drape reaches the full length, unfolded state: wherein said upper end has a first width and said lower end has a second width; wherein said first width is less than said second width to substantially conform to the radiation shield toward the top of the drape when the drape reaches full length, unfolded state;
   wherein said upper end has a first width and said lower end has a second width;
   wherein said first width is less than said second width to substantially conform to the radiation shield;
   wherein said wall is circumferentially continuous, tubular wall; and further including at least one second fastener releasably fixing said wall in said reduced length, folded state.

\* \* \* \* \*